(12) United States Patent
Kovacs et al.

(10) Patent No.: US 8,050,737 B2
(45) Date of Patent: Nov. 1, 2011

(54) METHOD AND MEDICAL APPARATUS FOR MEASURING PULMONARY ARTERY BLOOD FLOW

(75) Inventors: Gabor Kovacs, Graz (AT); Horst Olschewski, Graz (AT); Gert Reiter, Graz (AT); Ursula Reiter, Graz (AT); Rainer Kurt Rienmueller, Graz (AT)

(73) Assignee: Siemens Aktiengesellschaft, Munich (DE)

( * ) Notice: Subject to any disclaimer, the term of this patent is extended or adjusted under 35 U.S.C. 154(b) by 512 days.

(21) Appl. No.: 12/325,317

(22) Filed: Dec. 1, 2008

(65) Prior Publication Data
US 2009/0143667 A1 Jun. 4, 2009

(30) Foreign Application Priority Data
Nov. 30, 2007 (DE) .......................... 10 2007 057 553

(51) Int. Cl.
*A61B 8/06* (2006.01)
*A61B 5/055* (2006.01)
(52) U.S. Cl. ......... 600/419; 600/410; 600/437; 600/454
(58) Field of Classification Search ........................ None
See application file for complete search history.

(56) References Cited

U.S. PATENT DOCUMENTS

| | | | | |
|---|---|---|---|---|
| 5,687,731 A * | 11/1997 | Ragozin et al. | ............... | 600/485 |
| 5,701,898 A * | 12/1997 | Adam et al. | .................. | 600/454 |
| 5,830,143 A * | 11/1998 | Mistretta et al. | ............... | 600/420 |
| 5,836,884 A * | 11/1998 | Chio | ............................ | 600/485 |
| 6,526,117 B1 * | 2/2003 | Okerlund et al. | ................. | 378/8 |
| 2003/0166999 A1 * | 9/2003 | Liu et al. | ...................... | 600/410 |

OTHER PUBLICATIONS

Galie "Guidelines on diagnosis and treatment of pulmonary arterial hypertension" The Task Force on Diagnosis and Treatment of Pulmonary Arterial Hypertension of the European Society of Cardiology European Heart Journal 2004; 25(24): p. 2243-2278; Elsevier, ESC Guidelines, European Society of Cardiology.
Olschewski et al.: "Diagnosis and therapy of chronic pulmonary hypertension"Pncumologic 2006; 60(12): p. 749-771, Leitlinic.
Chemla et al.: "Haemodynamic evaluation of pulmonary hypertension" Eur Respir J 2002; 20: p. 1314-1331, European Respiratory Journal, ISSN 0903-1936.
Denton, et al.: "Comparison of Doppler Echocardiography and Right Heart Catheterization to Assess Pulmonary Hypertension in Systemic Sclerosis" British Journal of Rheumatology 1997; 36: p. 239-243, UK.

(Continued)

*Primary Examiner* — Unsu Jung
*Assistant Examiner* — Lawrence Laryea
(74) *Attorney, Agent, or Firm* — Schiff Hardin LLP

(57) ABSTRACT

In a method and apparatus for examination and evaluation of a blood flow in a pulmonary artery of a patient, measurement data are recorded, from which at least a part of the blood flow in the pulmonary artery is able to be re-constructed at least two-dimensionally in a plane defined by a longitudinal axis of the pulmonary artery and by an anterior-posterior direction, including at least at several diastolic points in time in the course of a heart cycle, after a closure of the pulmonary valve. The number of diastolic points for which an asymmetry in relation to the longitudinal axis of the pulmonary artery in the anterior-posterior direction exists is determined. A measure is then determined that characterizes how long, after the closure of the pulmonary valve, the aforementioned asymmetry exists.

14 Claims, 4 Drawing Sheets

OTHER PUBLICATIONS

Laaban et al.: "Noninvasive Estimation of Systolic Pulmonary Artery Pressure Using Doppler Echocardiography in Patients with Chronic Obstructive Pulmonary Disease" Chest 1989; 96: 1258-1262, http://chestjournal.org/cgi/content/abstract/96/6/1258.

Hinderliter et al.: "Effects of Long-term Infusion of Prostacyclin (Epoprostenol) on Echocardiographic Measures of Right Ventricular Structure and Function in Primary Pulmonary Hypertension" Circulation 1997; 95: 1479-1486; American Heart Association; http://circ.ahajournals.org/cgi/content/full/95/6/1479.

King et al.: "Intraventricular septal configuration as a predictor of right ventricular systolic hypertension in children: a cross-sectional echocardiographic study" Circulation 1983; 68: 68-75; Diagnostic Methods, Congenital Heart Disease.

Roeleveld et al.: "Intraventricular Septal Configuration at MR Imaging and Pulmonary Arterial Pressure in Pulmonary Hypertension" Radiology 2005; 234: 710-717.

Kitakabe et al.: "Noninvasive evaluation of pulmonary hypertension by a pulsed Doppler technique" Circulation 1983; 68: 302-309; Others; 1983; Diagnostic Methods, Congenital Heart Disease.

Mousseaux et al.: "Pulmonary arterial resistance: noninvasive measurement with indexes of pulmonary flow estimated at velocity-encoded MR imaging-preliminary experience" Radiology 1999; 212 (3): 896-902.

Laffon et al.: "Non-invasive assessment of pulmonary arterial hypertension by MR phase-mapping mapping method" J Appl Physiol 2001; 90: 2197-2202.

Laffon et al.: A computed method for noninvasive MRJIassessment of pulmonary arterial hypertension: J Appl Physiol 2004; 96: 463-468; Others; 2004.

Kondo et al.: "Pulmonary Hypertension: Pulmonary Flow Quantification and Flow Profile Analysis with Velocity-encoded Cine MR Imaging" Radiology 1992; 183: 751- 758; Others; 1992.

Reiter et al.: "MR vector field measurement and visualization of normal and pathological time-resolved three-dimensional cardiovascular blood flow patterns" J Cardiovasc Magn Reson 2007; 9: 237-238; Others, Friday Poster Abstracts.

Mohiaddin et al.: "Visualization of flow by vector analysis of multidirectional cine MR velocity mapping" Journal of computer assisted tomography 1994; 18: 383-392; Others; 1994.

* cited by examiner

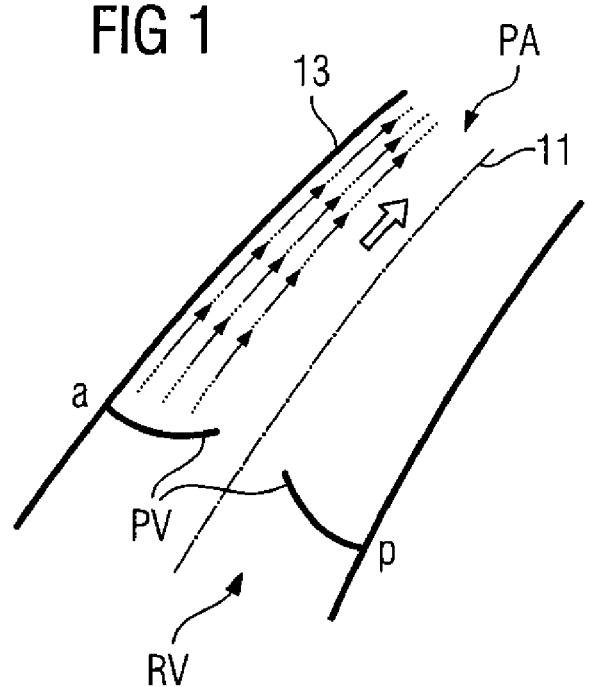
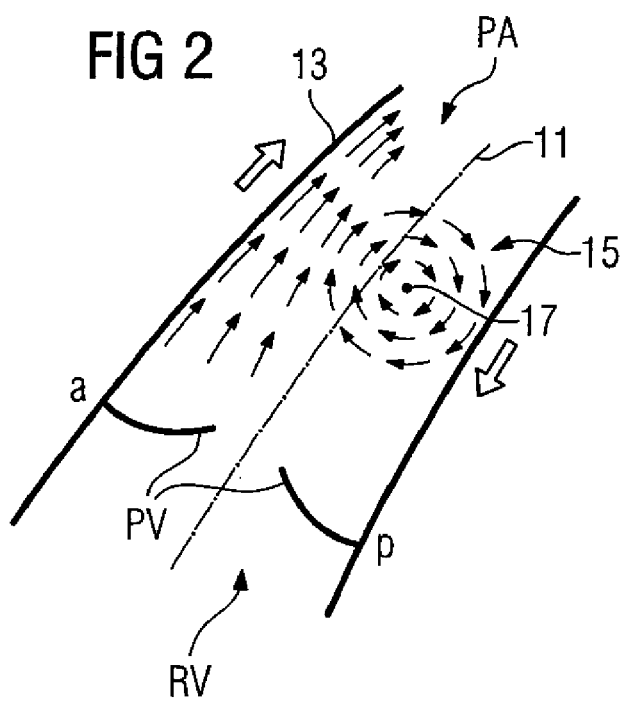

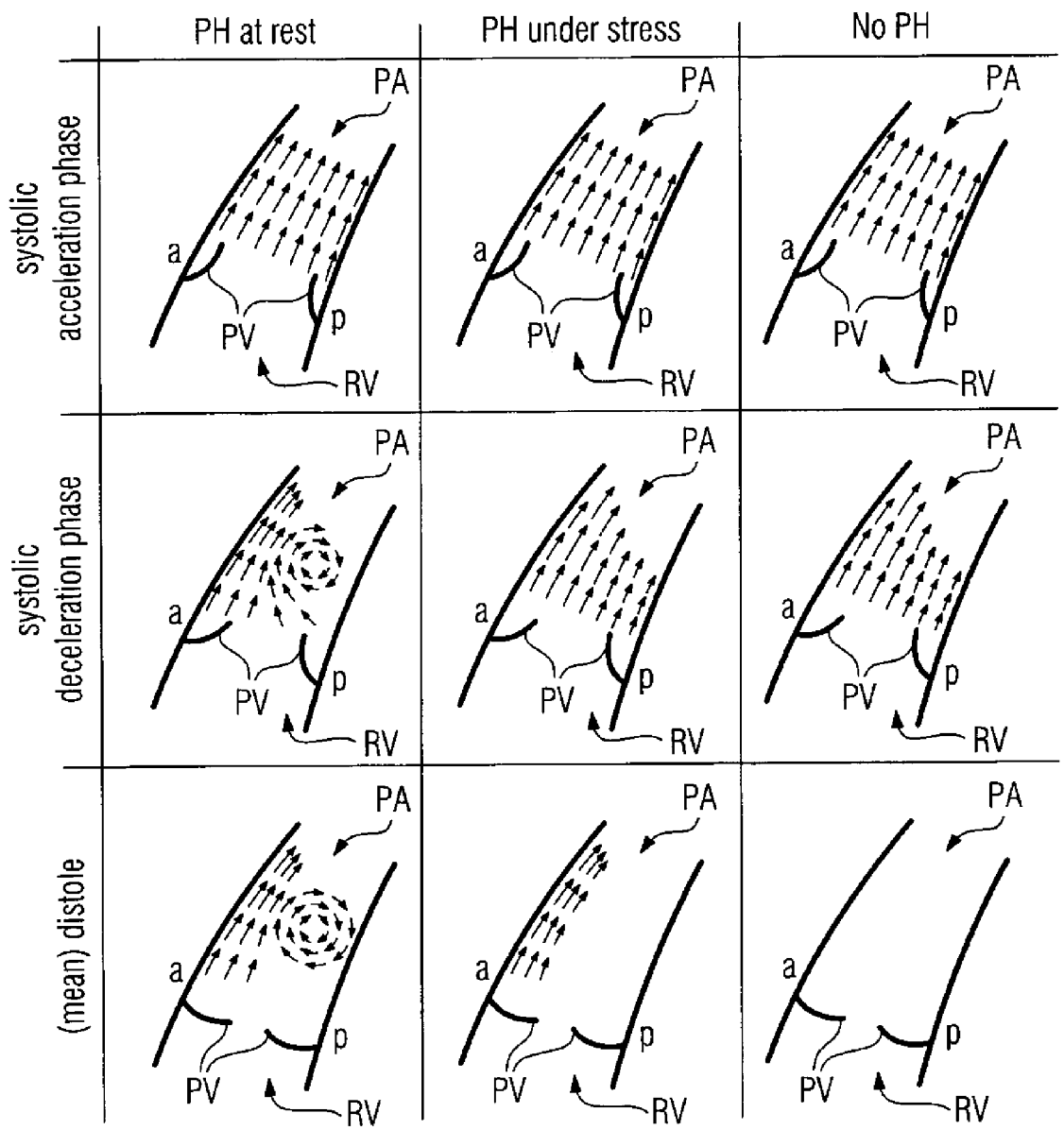

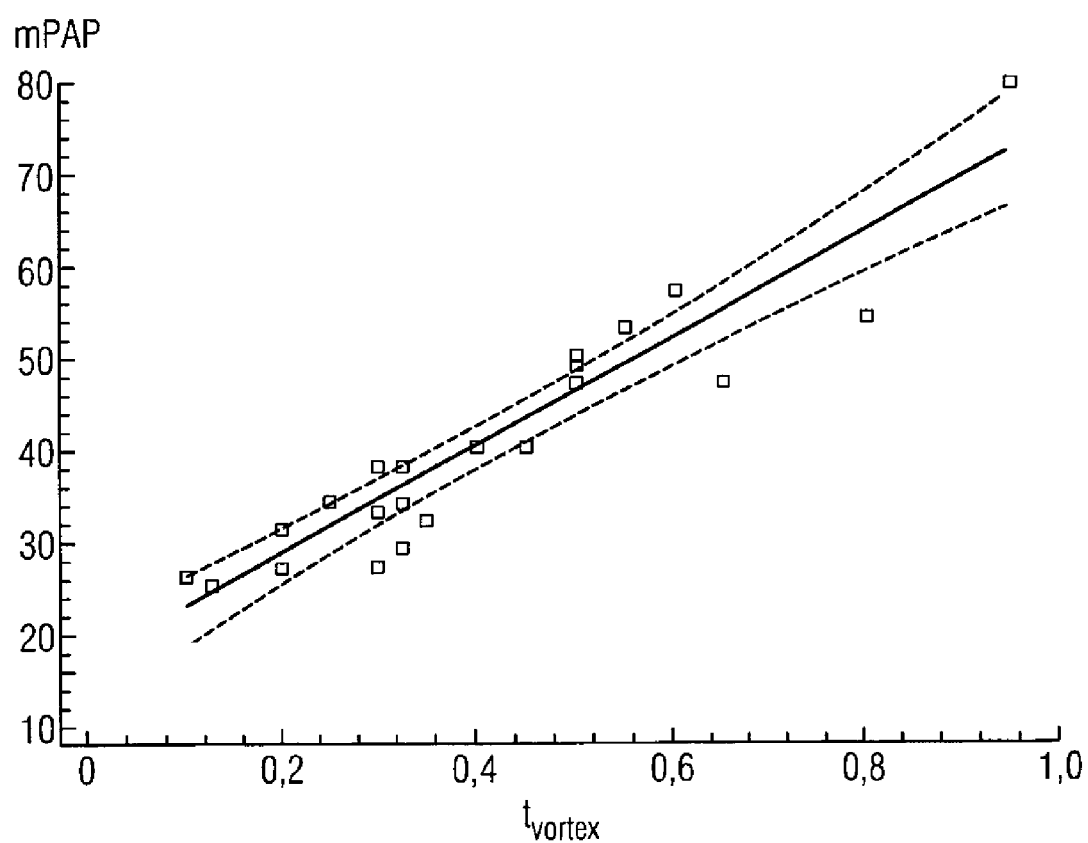

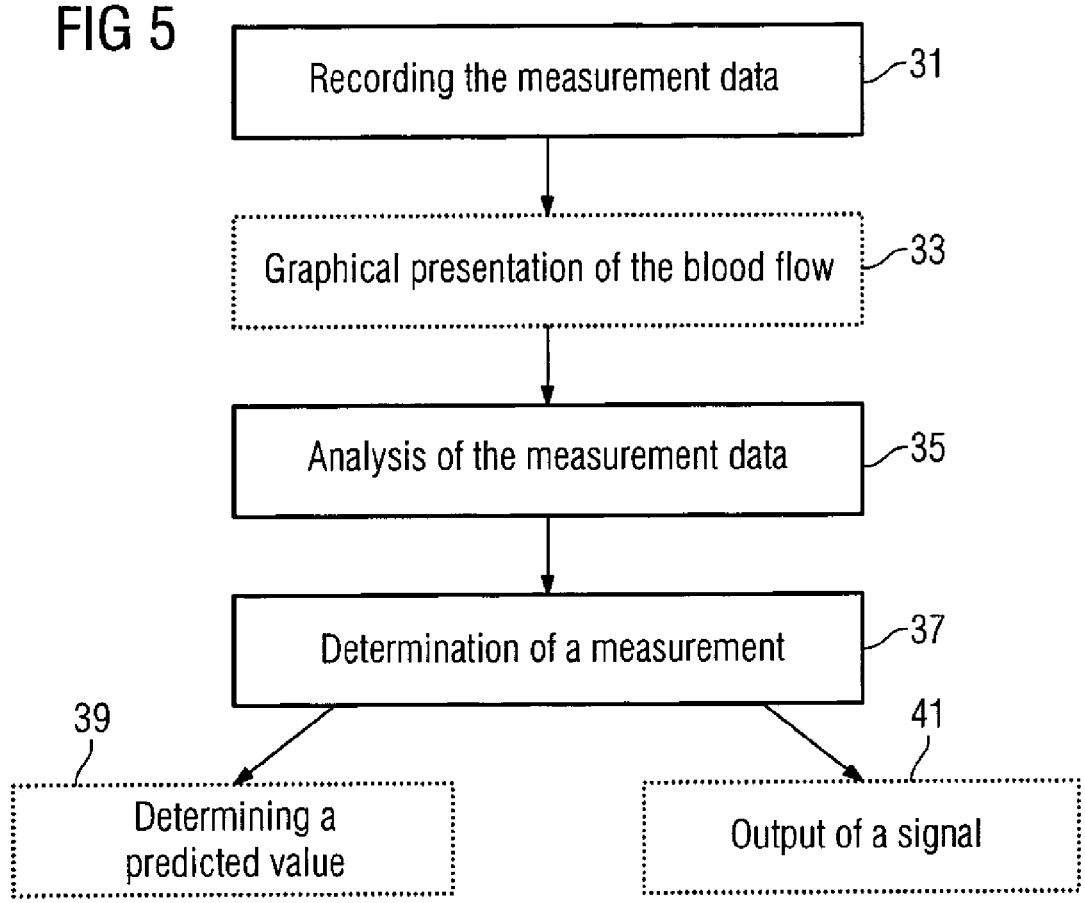
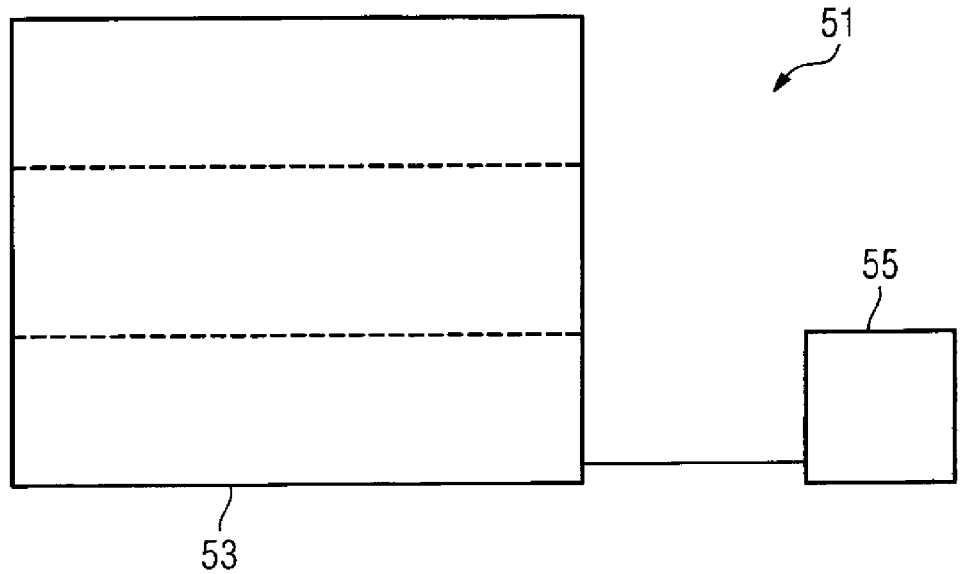

METHOD AND MEDICAL APPARATUS FOR MEASURING PULMONARY ARTERY BLOOD FLOW

BACKGROUND OF THE INVENTION

1. Field of the Invention

The present invention concerns a method for examining a human or animal body with regard to a blood flow in the pulmonary artery. In addition the invention concerns a medical imaging apparatus for implementing such a method. Such a method is especially used in the examination of patients with a pulmonary hypertension or with a suspected pulmonary hypertension or with a pulmonary hypertension occurring when the body is under stress.

2. Description of the Prior Art

Pulmonary hypertension (abbreviated "PH" below) is an illness characterized by an increase in the pulmonary artery pressure. Pulmonary arterial hypertension (abbreviated "PAH" below) is a subgroup of PH. The definition of PAH has been established in the usual guidelines. It relates to the mean pulmonary artery pressure (mPAP) and not to the systolic pulmonary artery pressure (sPAP) and to the exclusion of basic conditions such as serious lung or left heart diseases. PAH exists if the mean pulmonary artery pressure (mPAP) exceeds 25 mm Hg at rest or 30 mm Hg under stress. By comparison, the normal pulmonary pressure at rest is below 21 mm Hg. The prognosis of the PH is bad regardless of its genesis, especially if the diagnosis is made late.

Overview articles and guidelines about pulmonary hypertension can be found in the publications Galie N et al., "Guidelines on diagnosis and treatment of pulmonary arterial hypertension", The Task Force on Diagnosis and Treatment of Pulmonary Arterial Hypertension of the European Society of Cardiology, Eur Heart J 2004; 25(24): 2243-2278 and Olschewski H et al., "Diagnosis and therapy of chronic pulmonary hypertension" Pneumologie 2006; 60(12): 749-771.

A right heart catheter examination (swan-neck catheter) is currently seen as the "gold standard" method of examination for the determination of pulmonary artery pressure and thereby for the diagnosis of pulmonary hypertension. This examination is invasive however and must be carried out by experienced personnel to obtain reliable data and to keep the risks low. The costs of such an examination are high.

The publications Chemla D et al. "Haemodynamic evaluation of pulmonary hypertension" Eur Respir J 2002; 20: 1314-1331, Denton C P et al. "Comparison of Doppler Echocardiography and Right Heart Catheterization to Assess Pulmonary Hypertension in Systemic Sclerosis" Br J Rheumatology 1997; 36: 239-243, Laaban J P et al. "Estimation of Systolic Pulmonary Artery Pressure Using Doppler Echocardiography in Patients with Chronic Obstructive Pulmonary Disease" Chest 1989; 96: 1258-1262, and Hinderliter A L et al. "Effects of Long-term Infusion of Prostacyclin (Epoprostenol) on Echocardiographic Measures of Right Ventricular Structure and Function in Primary Pulmonary Hypertension" Circulation 1997; 95: 1479-7486 deal with methods such as the color doppler echocardiography method with which the systolic pulmonary artery pressure (abbreviated below "sPAP") can be determined from the maximum regurgitation velocity of a tricuspid insufficiency. This method is currently used as a screening examination for establishing pulmonary arterial hypertension. For patients with PAH the sensitivity is around circa 90% and the specificity is around 67% to 75%. The accuracy of the estimation in a healthy control population is however not known. In addition the practice of computing the mPAP from the sPAP is not established.

Other alternative non-invasive methods are subordinate to color doppler echocardiography.

A method is known from the publication Kitakabe A I et al. "Noninvasive evaluation of pulmonary hypertension by a pulsed Doppler technique" Circulation 1983; 68: 302-309 in which the acceleration time of the blood stream is determined with the aid of color doppler echocardiography and used as the correlate to the logarithm of the mPAP.

A method is known from the publication Mousseaux E et al. "Pulmonary arterial resistance; noninvasive measurement with indexes of pulmonary flow estimated at velocity-encoded MR imaging—preliminary experience" Radiology 1999; 21 2(3): 896-902 in which inter alia the maximum changes over time of the blood flow is determined from one-dimensional magnetic resonance phase-contrast flow measurements in the pulmonary artery as the correlate to pulmonary vascular resistance.

Known from the publications Laffon E et al. "Noninvasive assessment of pulmonary arterial hypertension by MR phasemapping method" J Appl Physiol 2001; 90: 2197-2202, and Laffon E et al. "A computed method for noninvasive MRI assessment of pulmonary arterial hypertension" J Appl Physiol 2004; 96; 463-468 are methods in which the pressure wave velocity and the maximum blood stream velocity can be measured with the aid of one-dimensional magnetic-resonance phase-contrast flow quantities in the pulmonary artery and an optimum functional relationship to mPAP determined. These types of results were not able however to be reliably reproduced by other working groups.

In the publication Kondo C et al. "Pulmonary Flow Quantification and Flow Profile Analysis with Velocity-encoded Cine MR Imaging" Radiology 1992; 183: 751-758 the relationship is demonstrated that patients with a PH exhibit a greater proportion of retrograde blood flow in the pulmonary artery.

The publication Mohiaddin R H et al. "Visualization of flow by vector analysis of multidirectional cine MR velocity mapping", Journal of computer assisted tomography 1994, 18: 383-392 describes how, in patients with pulmonary hypertension in the diastole, a backwards-directed flow in the pulmonary artery is detectable.

All the publications cited represent small explorative series. Most of the methods described therein have not been able to establish themselves.

SUMMARY OF THE INVENTION

An object of the invention is to provide a method that supports a user in examinations within the context of diagnosis of pulmonary hypertension in a reliable manner and that can be implemented substantially independently of the user. Furthermore it is an object of the invention to specify a medical imaging apparatus with which such a method can be implemented.

The method in accordance with the invention, for examination an evaluation of a human or animal body in relation to a blood flow in an pulmonary artery, includes the following steps:

(a) Recording measurement data from which at least a part of the blood flow in the pulmonary artery is able to be reconstructed at least two-dimensionally in a plane spanned by a longitudinal axis of the pulmonary artery and by an anterior-posterior direction, including at least at several diastolic times in the course of a heart cycle, after a closure of the pulmonary valve, (b) Analysis of the measurement data in respect of at how many of the at least several diastolic times in the flow behavior of the blood flow of pulmonary artery an asymmetry as regards the longitudinal axis of the pulmonary artery in the anterior-posterior direction exits, (c) Determining a measure that characterizes how long after the closure of the pulmonary valve in the flow behavior of the blood flow of the pulmonary artery asymmetry as regards the longitudinal axis of the pulmonary artery in the anterior-posterior direction exists; and (d) Making the measure available as an output.

The basis of the method is that conclusions can be drawn from a specific flow behavior of the blood flow in the pulmonary artery about whether or not pulmonary hypertension is present in the patient under examination. Changes in the blood flow can be caused by pulmonary hypertension which are reflected in the three-dimensional flow pattern in the pulmonary artery. In this case it has been recognized that an asymmetry in the flow behavior of the blood flow as regards the longitudinal axis of the pulmonary artery can be used to obtain significantly more informative results than with known methods, such as those described at the outset for example.

More precisely it was recognized in this case that the length of time for which a specific flow behavior exists in the pulmonary artery can be correlated especially well with the presence of a pulmonary arterial hypertension. The period in such cases can be described with a measure which characterizes the length of the period. In this case the interval which is the length of time that a specific flow behavior obtains in the pulmonary artery after the closure of the pulmonary valve, above all during the diastole, is of especial significance. For example after determination of the measure a signal is created if the measure exceeds a specific threshold value. In this manner a user is made aware of the possible existence of a pulmonary hypertension. In particular the measure is determined by evaluating the number of those times from the at least several diastolic time at which the asymmetric flow behavior was present. The measure determined by the method for examining the blood flow in the pulmonary artery can give a user important information within the framework of diagnosis of a PH. To this extent the method can support the diagnosis in relation to a pulmonary hypertension.

The method can also be used with other medical diseases which are associated with the risk of a PH. In this way patients with heart disease (e.g. chronic left heart diseases, right heart insufficiency, congenital, acquired and postoperative defects), with chronic obstructive pulmonary diseases (COPD), with thromboembolisms can be examined. In such cases the method can be used for manifest diseases in each case as well as for diagnosis of suspected disease and diagnosis to exclude disease.

In the described method above, all the individual steps—as for example the step of recording of measurement data or the step of analyzing measurement data and/or the step of determining the measure—can be executed automatically or semi-automatically in interaction with a user. In this way the method can be executed to a large extent independently of a user. For example the measurement data can be recorded with a magnetic resonance examination, especially with a phase-contrast measurement. For example a flash (fast low-angle shot)-based phase-contrast measurement can be used as the magnetic resonance sequence. In this way the measurement data obtained is far more constant and independent of a user who is conducting the examination, compared for example to a conventional color doppler echocardiography examination undertaken with an ultrasound device. Although such an examination is in principle also possible, it can be rendered more difficult for example by anatomical changes or by peculiarities of the examination site such as a lung overinflation for example. In principle all diagnostic modalities which allow a two-dimensional and especially three-dimensional presentation of blood flow fields can be employed for data recording.

In addition the recording of the measurement data can be undertaken without application of contrast media, which enhances safety for a patient. Overall the method is fast, simple and risk-free.

The evaluation of the measurement data itself and the determination of the measure can be implemented fully automatically in such cases or for example such that parts of the method steps are undertaken in interaction with a user. For example a user can identify particular areas in the pulmonary artery which have a particular flow pattern, so that the further evaluation can be carried out automatically on this basis.

This enables screening examinations to be implemented in a simple manner providing a user with reliable intermediate results with which a user can assess the existence of a pulmonary hypertension as likely or less likely. The prognosis of pulmonary hypertension, which is bad regardless of its genesis, especially if the diagnosis is conducted late, can be improved In this way without having to have recourse to invasive examination methods.

The measurement data is recorded in such cases such that at least a part of the blood flow in the pulmonary artery is able to be reconstructed in the plane defined by the longitudinal axis of the pulmonary artery and by the anterior-posterior direction. This plane essentially corresponds to a sagittal plane or a sagittal-oblique plane. The recording of the measurement data can in such cases for example also be undertaken in transversal planes, such that a reconstruction of the blood flow can subsequently be undertaken in a sagittal or sagittal-oblique plane.

In an embodiment, during the step of recording the measurement data the measurement data is recorded such that from the measurement data at least one part of the blood flow in the pulmonary artery is able to be reconstructed three-dimensionally. In this way the detection of the asymmetry with regard to the longitudinal axis of the pulmonary artery in the anterior-posterior direction is possible more exactly and more quickly, since three-dimensional data of the blood flow is available in order to detect a specific flow behavior. The danger of overlooking a specific flow behavior since a two-dimensional plane may possibly not run exactly through the area with the characteristic flow behavior of the blood flow is in this way significantly less.

In an embodiment, during the step of recording the measurement data the measurement data is recorded distributed over the entire heart cycle. This enables the time gradient of the at least one part of the blood flow over the entire heart cycle to be determined from the recorded measurement data. This means that in addition to the at least several diastolic points in time, systolic points in time are also included. The step of analyzing the measurement data can In this way be executed more exactly since in addition to the diastolic time range of the heart cycle, the systolic range of the heart cycle is now also available.

Preferably during analysis of the measurement data the blood flow in the pulmonary artery is examined to establish at how many diastolic points in time there is a flow in the anterior third of the pulmonary artery in direction of movement of the pulmonary artery which is greater than a flow in the posterior third of the pulmonary artery. In such cases flow differences between the anterior third and the posterior third which lie below a threshold value remain unconsidered. This can for example be implemented by an algorithm for evaluation of smaller flows not being recorded and only flows as from a certain size being taken into account. This means that smaller flow differences, which also occur in the electrophysiological case in the blood flow, are not taken into consideration. Especially, if after closure of the pulmonary valve a marked flow difference between the anterior third of the pulmonary artery and the posterior third of the pulmonary artery is present over a certain period of time, this indicates the presence of a pulmonary hypertension.

In an advantageous embodiment, during the step of analyzing the measurement data, the blood flow in the pulmonary artery is examined to establish at how many of the at least several diastolic points in time a vortex is present which has a vortex axis which lies essentially transverse to the longitudinal axis of the pulmonary artery and transverse to the anterior-posterior direction. This type of vortex is an especially clear form of the asymmetry in the flow behavior of the blood flow in the pulmonary artery. In such cases, in an area which faces the anterior wall of the pulmonary artery the vortex has a flow in the direction of movement of the pulmonary artery, while the vortex in an area which faces the posterior wall of the pulmonary artery has a flow against the direction of movement of the pulmonary artery. In addition the vortex has a first transverse component which is directed in the posterior-anterior direction, as well as a second transverse component which is directed in the anterior-posterior direction. The first transverse component lies in this case closer to the pulmonary valve than the second transverse component. It has especially been established that the presence of such a vortex in the blood flow of the pulmonary artery, especially at a diastolic point in time, gives a clear indication of a pulmonary hypertension under rest conditions. Usually this type of vortex already occurs during the systolic phase. Its existence extends however also into the diastolic phase if a pulmonary hypertension exists under rest conditions.

However merely the presence of an asymmetrical flow along the longitudinal axis of the pulmonary artery without vortex formation can count as a clear indication that the patient to be examined exhibits a stress-induced pulmonary hypertension.

The measure that characterizes the period of time at which a specific flow behavior exists in the pulmonary artery—such as an anterior-posterior asymmetry or a vortex—can be determined in a simple manner by the number of times at which the specific flow behavior exists in the blood flow of the pulmonary artery being related by the overall number of the recorded times. As an alternative to this for example the absolute number of the points in time can be used as a measure at which the specific flow behavior exists in the blood flow of the pulmonary artery. In another variant for example the absolute period or the relative period can be determined relative to the overall period of the heart cycle during which the specific flow behavior exists, such as for example the described anterior-posterior asymmetry in the flow behavior of the pulmonary artery or the described vortex.

In a further advantageous embodiment variant a predicted value can be determined with the use of the determined measure which characterizes the pulmonary blood pressure. In this way the method is developed into a method for examination of a human or animal body in relation to a blood pressure. In particular a prediction value for the average arterial pulmonary blood pressure can be determined. This can be done for example using a correlation held in a memory of a processing unit. Examinations have revealed in such cases that the period during which the specific flow behavior exists correlates well with a measured mean pulmonary arterial blood pressure in a linear or logarithmic manner. The method is sensitive, fast, simple and risk-free. It can be used both as a screening method, for follow-ups as well as possibly as a replacement for an invasive examination.

In an embodiment variant, after the step of recording the measurement data, a graphic presentation of the blood flow in the pulmonary artery is generated. The step of analyzing the measurement data can then be undertaken with the aid of or on the graphic representation of the blood flow in the pulmonary artery. Graphic representations of the time-resolved flow fields can for example visualize the blood flow with the aid of a vector field, especially with the aid of a color-coded vector-field. Methods for this are disclosed for example in the Publication by Reiter G et al. "MR vector field measurement and visualization of normal and pathological time-resolved three-dimensional cardiovascular blood flow patterns" J Cardiovasc Magn Reson 2007; 9: 237-238. Such methods can be implemented by software.

The inventive medical imaging apparatus has a processor unit for control of the medical imaging apparatus and for evaluation of recorded measurement data and is embodied for implanting the method as described above, and all embodiments thereof. The processor unit in this case can be implemented as a single processor unit or also be divided up into one or more subunits, of which each subunit assumes specific control and/or evaluation tasks.

BRIEF DESCRIPTION OF THE DRAWINGS

FIG. 1 is a schematic diagram of the blood flow in the pulmonary artery which exhibits a characteristic, asymmetrical flow behavior with regard to the anterior-posterior direction.

FIG. 2 is a schematic diagram of the blood flow which exhibits a characteristic vortex for the existence of a pulmonary hypertension.

FIG. 3 is a schematic overview of the characteristic behavior of the blood flow for a healthy person, for a patient with pulmonary hypertension and for a patient with stress-induced pulmonary hypertension.

FIG. 4 is a correlation between the period of the presence of a characteristic vortex field and a measured mean pulmonary arterial blood pressure.

FIG. 5 is a schematic overview of method steps of an embodiment of the inventive method.

FIG. 6 is a schematic overview of a medical imaging apparatus, with which embodiments of the inventive method can be executed.

DESCRIPTION OF THE PREFERRED EMBODIMENTS

FIG. 1 shows a schematic diagram of the blood flow in the pulmonary artery PA at a diastolic point in time after closure of the pulmonary valve PV with a characteristic asymmetrical flow behavior. The asymmetry relates to a difference in the flow behavior in the anterior-posterior direction in relation to the longitudinal axis 11 of the pulmonary artery, RV identifies the outflow tract in the right ventricle, the letters a and p the anterior or the posterior direction respectively. The blood flow in the pulmonary artery PA is consequently shown in an essentially sagittal plane. It can clearly be seen that the blood flow in the anterior third of the pulmonary artery PA is parallel to the anterior wall 13 of the pulmonary artery PA. This blood flow is considerably stronger than the blood flow in the posterior third of the pulmonary artery PA. If such a flow behavior exists over a certain period during the diastole after closure of the pulmonary valve PV, this indicates that a patient to be examined exhibits at least one stress-induced pulmonary hypertension.

FIG. 2 shows a schematic diagram of the blood flow in the pulmonary artery PA in the same plane, with the blood flow this time having a characteristic vortex 15, of which the vortex axis 17 points essentially perpendicular to the longitudinal axis of the pulmonary artery PA and essentially perpendicular to the anterior-posterior direction. In the anterior area of the pulmonary artery PA the vortex 15 features components in the flow direction of the pulmonary artery PA, while in the posterior area of the pulmonary artery PA the vortex 15 features components which point in the opposite direction of flow of the pulmonary artery PA. In addition the vortex 15 exhibits a clearly marked first transverse component from anterior to posterior and a clearly marked second transverse component from posterior to anterior. The second transverse component in this case lies closer to the pulmonary valve PV than the first transverse component. If this type of vortex 15 is present for a certain period during the diastole after closure of the pulmonary valve PV, this indicates that the patient under examination has a pulmonary hypertension under rest conditions. Usually such a vortex already occurs in the systole.

The evidence of such a correlation has been investigated in a study. In this study 38 patients with suspected pulmonary hypertension or with an already proven pulmonary hypertension were investigated. With all patients both a right heart catheterization and also a magnetic resonance phase-contrast examination of the pulmonary artery was carried out. Of the 38 patients, 22 patients exhibited a pulmonary hypertension under rest conditions and 13 patients merely exhibited a stress-induced pulmonary hypertension. Three patients exhibited a normal mPaP under rest conditions and under stress. Ten healthy comparison persons without a previous history with a cardiovascular or pulmonary disease were likewise subjected to an MR phase-contrast examination of the pulmonary artery. Normal left and right ventricular functional parameters were checked on the basis of a conventionally EKG triggered cine MR phase-contrast imaging.

Based on the right heart catheter examination the 38 patients with a suspected or an already verified pulmonary hypertension can be classified into different groups, namely into patients without a pulmonary hypertension, into patients with a pulmonary hypertension under rest conditions as well as into patients with a stress-induced pulmonary hypertension.

The magnetic resonance imaging was undertaken EKG-triggered on a 1.5 Tesla appliance (MAGNETOM Sonata, Siemens) with a 6-channel heart coil. The examination was carried out in a supine position of the subject or patient.

In order to record velocity field measurement data the pulmonary artery was sampled seamlessly in the orientation of the right ventricular outflow tract by two-dimensional, retrospectively EKG-triggered, flashed-based (flash=fast low angle shot) phase-contrast sequences. The right ventricular outflow tract was covered with the two-dimensional phase-contrast measurements with velocity encoding in all spatial directions (1 to 4 measurements, duration appr. 1 to 5 minutes).

Velocity data was able to be recorded with a simple four-point velocity encoding scheme. For presentation the velocity encoding was set to 90 cm/s in all directions and adapted if necessary if aliasing was observed in the main stem of the pulmonary artery.

Further parameters which were employed in the protocol used, are for example a field-of-view of 234–246×340 mm², an image matrix of 96–114×192 pixels (interpolated to 192–228×384), a flip angle of 15°, 89 ms repetition time, reconstruction of 20 heart phases, 4.1 ms echo time and 451 Hz/pixel bandwidth. A GRAPPA technique (GRAPPA stands for "generalized autocalibration partially parallel acquisition") with a parallel acquisition factor of 2 was used to set the imaging time per layer between 22 and 23 heartbeats, so that the measurements could be undertaken while the breath was being held during inspiration. If persons being examined were not capable of holding their breath, the examination was undertaken with the patient breathing freely and with multiple averaging, for example with triple averaging in order to reduce movement artifacts.

The computation of the velocity field from the phase-contrast images and also the process visualization and the analysis of the velocity field was able to be undertaken with known software. Such software is described for example in the publication Reiter G et al. "MR vector field measurement and visualization of normal and pathological time-resolved three-dimensional cardiovascular blood flow patterns" J Cardiovasc Magn Reson 2007; 9: 237-238.

Velocity vectors were shown as color-coded vectors three-dimensionally in space. Length and color of the vector represent the amount of the velocity, the direction of the vector in the presentation of the direction of the velocity. Three-dimensional velocity fields were projected with the aid of velocity vectors onto a corresponding anatomical presentation. The suppression of noisy pixels and a variable thinning of the vector field allow an interpretation of the blood flow within the anatomical context.

Different parameters were analyzed on the basis of the blood flows determined. For example an analysis was undertaken of whether an existence of vortexes in the main flow direction was present in the main stem of the pulmonary artery, as is shown for example in FIG. 2. If there was a vortex an analysis was undertaken of whether concentric, ring or spiral-shaped curve movements in the blood flow of the pulmonary artery were present, along which the velocity vectors moved tangentially. In particular the relative period $t_{vortex}$, which specifies for how long such a vortex exists, was determined. In this case the number of heart phases in which such a vortex existed was divided by the total number of heart phases in order to determine $t_{vortex}$.

In such cases it was observed that a vortex formation of the blood arose along the longitudinal axis of the pulmonary artery, if a pulmonary hypertension under rest conditions existed in the examined person. Persons without a pulmonary hypertension did not exhibit any of these vortex formations.

For example an analysis was likewise conducted of whether in the diastolic phase movement lines of the blood flow existed upwards along the anterior wall of the main stem of the pulmonary artery. Such behavior of the blood flow is typically shown in FIG. 1. It was consequently analyzed whether a blood flow along the front wall of the pulmonary artery existed during the diastole which does not exist on the posterior wall of the pulmonary artery or existed to a lesser extent. As in the case of the detection of vortexes, also in the case of the detection of such a flow behavior the relative period $t_{streamline}$ can be determined during which this flow behavior is present. The relative period $t_{streamline}$ can be computed in a similar manner.

In such cases it has been shown that such flow behavior correlates well with the presence of a stress-induced pulmonary hypertension. Persons with a normal pulmonary blood pressure exhibit neither a characteristic vortex formation nor a characteristic asymmetric behavior in the blood flow of the pulmonary artery during the diastole.

FIG. 3 shows the situation once again with reference to a schematic overview with nine small schematic diagrams. The drawings depicted show schematically typical striking features in the blood flow for different respective basic diseases and for healthy subjects.

The first, left column shows the typical flow behavior in the blood flow of the pulmonary artery at three different points in time in the heart cycle, for a person with a pulmonary hypertension under rest conditions (PH at rest). The second, center column shows the typical flow behavior, at the same point in time in the heart cycle, for a person with a stress-induced pulmonary hypertension (PH at stress" or PH during exercise). The third, right-hand column shows the typical flow behavior, at the same point in time in the heart cycle, for a person with a normal pulmonary blood pressure (no PH).

During the systole at an early point in time at which the blood flow increases (first, upper line, systolic acceleration phase) the blood flow for the three types only differs slightly (first line, left, center and right diagram).

During the systole at a later point in time, at which the blood flow reduces (second, center line, systolic deceleration phase), a person with a pulmonary hypertension at rest already exhibits the beginnings of a vortex formation and uniquely asymmetrical behavior in the blood flow of the pulmonary artery with regard to the longitudinal axis of the pulmonary artery in the anterior-posterior direction (second line, left-hand diagram).

At this point in time the blood flow in the pulmonary artery for a person with a stress-induced pulmonary hypertension and for a healthy person exhibits an asymmetrical flow behavior, but no significant difference (second line, center and right-hand diagram).

During the diastole—shown here during the mid diastole (third, lower line)—the person with a pulmonary hypertension at rest exhibits an asymmetrical flow behavior in the pulmonary artery and a vortex formation (third line, left-hand diagram). The person with a stress-induced pulmonary hypertension merely exhibits an asymmetrical flow behavior without vortex formation (third line, center diagram), whereas the person with a normal pulmonary blood pressure does not exhibit this asymmetrical flow behavior (third line, right-hand diagram).

FIG. 4 shows a diagram in which measured pulmonary arterial blood pressures of different patients are plotted against the relative time $t_{vortex}$. A clear correlation between the relative period and the measured pulmonary artery pressure can be shown. A linear regression line can be described in this specific case for example by the formula $$\text{MPAP}(\text{in mm Hg}) = 16.7 + 58.0 \times t_{vortex},$$

if $t_{vortex}$ is determined as described above. The correlation coefficient in this case amounts to 0.94.

From this type of correlation, which for example can be stored in a processor unit, a predicted value for the mean pulmonary arterial blood pressure can be obtained from the measured flow behavior. Other variables which identify the pulmonary arterial blood pressure, such as the systolic pulmonary arterial blood pressure or the pulmonary vessel resistance can be predicted in a similar way, possibly with a worse correlation. In this way it is possible to quantitatively evaluate the blood flow in the pulmonary artery and obtain medically informative results.

FIG. 5 shows a schematic diagram of the method steps executed in the method. In a first step (step 31) measurement data is recorded from which at least one part of the blood flow in the pulmonary artery is able to be reconstructed at least two-dimensionally in a plane which is essentially spanned by a longitudinal axis of the pulmonary artery and by an anterior-posterior direction. From the recorded measurement data the part of the blood flow is able to be reconstructed at least at a number of diastolic points in time in the course of a heart cycle after a closure of the pulmonary valve. In particular the blood flow is able to be reconstructed over the entire heart cycle.

In a further step (step 35) the measurement data is analyzed as to at how many of the at least several diastolic points in time in the flow behavior of the blood flow of the pulmonary artery an asymmetry in relation to the longitudinal axis of the pulmonary artery in the anterior-posterior direction is present. In particular the measurement data can be analyzed as to whether and for how long a vortex is present which has a vortex axis which lies essentially transverse to the longitudinal axis of the pulmonary artery and transverse to the anterior-posterior direction. Such a vortex represents an especially strong form of asymmetry in relation to the longitudinal axis of the pulmonary artery.

Advantageously before step 35 a reconstruction of the blood flow can be undertaken from the measurement data and a graphic presentation of the blood flow (step 33). Step 35 can subsequently be performed on the graphic presentation of the blood flow.

For example algorithms can be implemented for evaluation which evaluate the graphical presentation of the blood flow automatically or semi-automatically in interaction with a user in respect of the flow pattern sought. E.g. algorithms can be implemented which evaluate the flow behavior in the blood flow and detect vortexes with reference to their characteristic flow behavior or recognize an asymmetry in the flow behavior in the anterior third of the pulmonary artery by comparison with the posterior third. A vortex could for example be detected by analyzing whether self-contained lines are present along which the velocity vectors are tangential to each other.

Depending on the implementation of the algorithm a user can also mark specific areas according to which a characteristic blood flow behavior is to be evaluated. This enables algorithms to be implemented with less effort since less data must be evaluated. In an especially simple variant a user can also be shown the different images of a heart cycle, with a graphic presentation of the blood flow for example via a monitor and a user can mark those images on which a characteristic flow behavior has been detected earlier. A processor unit can subsequently on the basis of these markings determine the measure that characterizes how long the flow behavior to be detected exists in the blood flow and thus for example compute a predicted value for an average pulmonary arterial blood pressure.

Depending on the implementation of the evaluation and the analysis of the measurement data, a graphic presentation of the blood flow is not absolutely necessary however. For example it is also possible to compute flow values directly from the recorded measurement data and evaluate them without a graphic presentation.

In a further step (step 37) based on the analysis a measure is determined which characterizes how long after the closure of the pulmonary valve in the flow behavior of the blood flow of the pulmonary artery the asymmetry in relation to the longitudinal axis of the pulmonary artery in the anterior-posterior direction is present.

On the basis of the measure for example, as explained above, a predicted value for the mean pulmonary arterial blood pressure can be created (step 39). On the basis of the measure however information cam also be obtained as to whether a pulmonary hypertension under rest conditions or a stress-induced pulmonary hypertension have a specific probability of existing. As an alternative or in addition a signal can be output as soon as a measure exceeds a specific threshold value (step 41). This alerts a user to the fact that possibly a pathological behavior is present in relation to a pulmonary hypertension.

FIG. 6 shows a schematic diagram of the layout of a medical imaging apparatus 51, on which such a method can be implemented or executed. An imaging unit, for example a magnet 53 of a magnetic resonance device with associated hardware components, can in a known manner be employed for recording the measurement data. An ultrasound device can alternatively also be used for example as an imaging device or another imaging unit, with which data in relation to the blood flow can be recorded in the pulmonary artery.

The medical imaging apparatus 51 in this case has a processor unit 55, with which for example the imaging unit can be appropriately controlled. The method can be implemented in this processor unit 55.

This processor unit 55 in this case does not inevitably have to be embodied as a single self-contained unit, as is shown in FIG. 6. The processor unit 55 can also be distributed between a number of subunits and parts of the method can also be implemented on the respective subunits. For example a subunit can control the imaging unit while a further subunit of the processing unit is embodied such that the measurement data to be recorded can be evaluated automatically or in interaction with a user.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for examination and evaluation of a human or animal body in relation to a blood flow in a pulmonary artery (PA), comprising steps of:
   (a) recording measurement data, from which at least a part of the blood flow in the pulmonary artery (PA) is reconstructed at least two-dimensionally in a plane spanned by a longitudinal axis of the pulmonary artery (PA) and by an anterior-posterior direction, including a plurality of diastolic points in time in a course of a heart cycle, after a closure of a pulmonary valve (PV),
   (b) at least semi-automatically analyzing the measurement data to identify at how many diastolic points, among said plurality of diastolic points in time, an asymmetry exists as to the longitudinal axis of the pulmonary artery (PA) in the anterior-posterior direction;
   (c) at least semi-automatically determining a measure that characterizes how long after the closure of the pulmonary valve (PV) in a flow behavior of the blood flow of the pulmonary artery said asymmetry exists; and
   (d) making said measure available as an output.

2. The method as claimed in claim 1, further comprising during the step of recording the measurement data, recording the measurement data to allow at least a part of the blood flow in the pulmonary artery (PA) to be reconstructed three-dimensionally from the measurement data.

3. The method as claimed in claim 1, further comprising in the step of recording the measurement data, recording the measurement data distributed over an entire heart cycle, to allow a time gradient of the at least one part of the blood flow to be determined over the entire heart cycle from the recorded measurement data.

4. The method as claimed in claim 1, further comprising in the step of analyzing the measurement data, at least semi-automatically examining the blood flow to establish at which said diastolic points in time in an anterior third of the pulmonary artery a flow in a movement direction of the pulmonary artery exists that is greater than a flow in a posterior third of the pulmonary artery (PA).

5. The method as claimed in claim 1, further comprising in the step of analyzing the measurement data, at least semi-automatically examining the blood flow to establish at how many of the at least several diastolic points in time a vortex exists which has a vortex axis which is essentially transverse to the longitudinal axis of the pulmonary artery (PA) and transverse to the anterior-posterior direction.

6. The method as claimed in claim 1, further comprising determining the measure determining, for the at least several diastolic points in time, a number of points at which the flow behavior of the blood flow of the pulmonary artery (PA) at which asymmetry regarding the longitudinal axis of the pulmonary artery (PA) exists in the anterior-posterior direction and is related to a total number of the at least several diastolic points in time.

7. The method as claimed in claim 1, further comprising at least semi-automatically determining a predicted value characterizing a pulmonary blood pressure, from the measure via a stored correlation, by a linear correlation or logarithmic correlation.

8. The method as claimed in claim 1, further comprising generating a signal if the measure exceeds a threshold value.

9. The method as claimed in claim 1, further comprising generating a graphic presentation of the blood flow in the pulmonary artery after recording the measurement data, and analyzing the measurement data using the graphic presentation of the blood flow in the pulmonary artery.

10. The method as claimed in claim 9, further comprising generating the graphic presentation of the blood flow using a vector field.

11. The method as claimed in claim 1, further comprising recording the measurement data in a magnetic resonance examination.

12. The method as claimed in claim 11, further comprising recording the measurement data being recorded with a flash sequence-based phase contrast measurement.

13. The method as claimed in claim 1, further comprising recording the measurement data with an ultrasound examination method.

14. A medical imaging apparatus comprising:
   a measurement unit that interacts with a patient to obtain measurement data from the patient, from which at least a part of a blood flow in a pulmonary artery (PA);
   a computer that at least two-dimensionally reconstructs said blood flow in the pulmonary artery from said measurement data, in a plane defined by a longitudinal axis of the pulmonary artery and by an interior-posterior direction, that includes a plurality of diastolic points in time in a course of a heart cycle, after a closure of a pulmonary valve (PV); and
   a processor configured to at least semi-automatically analyze said measurement data to identify how many diastolic points, among said plurality of diastolic points in time, an asymmetry exists as to the longitudinal axis of the pulmonary artery in the interior-posterior direction, and to determine a measure that characterizes how long after said closure of the pulmonary valve in a flow behavior of the blood flow of the pulmonary artery said asymmetry exists, and to make said measure available as an output from said processor.

\* \* \* \* \*